US00PP10054P

United States Patent [19]

Challet

[11] Patent Number: Plant 10,054

[45] Date of Patent: Oct. 7, 1997

[54] CHRYSANTHEMUM PLANT NAMED 'CHAFEJE'

[75] Inventor: Jean Pierre Challet, Nuaille, France

[73] Assignee: Selection New Plant Sarl, Le Luc, France

[21] Appl. No.: 710,153

[22] Filed: Sep. 12, 1996

[51] Int. Cl.[6] ..... A01H 5/00

[52] U.S. Cl. ..... Plt./76

[58] Field of Search ..... Plt./76, 80, 81, Plt./82

[56] References Cited

PUBLICATIONS

"Mutation studies on Chrysanthemum", NBRI Newsletter, 1989, 16(1):2–3.

Datta, 1991, "Evaluation of recurrent irradiation on vegetatively propagated ornamentals: Chrysanthemum", J. Nuclear Agric. Biol., 20(2):81–86.

Banerji, et al., 1990, "Induction of somatic mutation in Chrysanthemum cultivar 'Anupam'", J. Nuclear Agric. Biol., 19:252–256.

Gosling, ed., 1979, "The Chrysanthemum Manual–6th edition," The National Chrysanthemum Society, Essex Telegraph Press, Ltd., London, pp.329–336.

Broertjes, et al., 1978, "Application of Mutation Breeding Methods In the Improvement of Vegetatively Propagated Crops", Elsevier Sci. Pub. Co., New York, pp. 162–175.

Gupta, et al., 1978, "Mutation breeding of Chrysanthemum II. Detection of gamma ray induced mutations in vM2", J. Nuclear Agric. Biol. 7(2):50–54.

Glazurina, et al., 1977, "Use of the method of artificial mutogenesis in the breeding of flower crops", Cytology and Genetics, vol. 11(3):42–45.

Das, et al., 1977, "Improvement of some vegetatively propagated ornamentals by gamma radiation", Indian J. Horticulture, 34(2):169–174.

Searle, et al., 1968, "Chrysanthemums the Year Round", Blanford Press, London, pp. 27–29, 320–327.

Dowrick, et al., 1966, "The induction of mutations in chrysanthemum using x–and gamma radiation", Euphytica, 15:204–210.

Broertjes, 1966, "Mutation breeding of Chrysanthemums", Euphytica, 15:156–162.

*Primary Examiner*—Howard J. Locker

*Attorney, Agent, or Firm*—Burns, Doane, Swecker & Mathis, L.L.P.

[57] ABSTRACT

A new and distinct Chrysanthemum cultivar named 'Chafeje' is provided. The new cultivar is a mutation that was created through gamma irradiation of the 'Chalecat' cultivar (U.S. Plant Pat. No. 9,463). Attractive very large double incurved blossoms of the pompon type are formed that are red in coloration. The incurving is particularly pronounced at the tips of the ray florets. The blossoms are very long lasting and keep their form for approximately two weeks. The response time of the flowers is approximately ten weeks. Recurrent profuse flower production throughtout the year is made possible. The plant possesses strong stems, forms attractive dark green leaves, and commonly assumes a height of approximately 40 to 45 cm. The blossom coloration contrasts nicely with the dark green foliage. The new cultivar is particularly suited for use in the production of a decorative pot Chrysanthemum that grows well when single stem or disbudded. No growth regulator is necessary to achieve the short to medium plant height.

1 Drawing Sheet

SUMMARY OF THE INVENTION

The present invention comprises a new and distinct cultivar of Chrysanthemum, botanically known as *Dendrenthema grandiflora*, and hereinafter is referred to by the cultivar name 'Chafeje'.

The new cultivar of the present invention was created through the gamma irradiation of the 'Chalecat' cultivar (U.S. Plant Pat. No. 9,463). The parent 'Chalecat' cultivar was formed by the crossing of the 'Siky' cultivar (non-patented in the United States) and the 'Prouesse' cultivar (non-patented in the United States).

During June 1980, at Saint Paul Lez Durance, France, groups of 1,000 rooted cuttings of the 'Chalecat' cultivar having an age of two weeks were irradiated with gamma rays through the packing boxes at rates of 1.8, 2.5 and 3.0 Krads. Following irradiation the plants were shipped to Nuaille, France, and were planted in 4 liter pots, were pinched, and were grown outside until September. The plants were next grown in greenhouses, were not disbudded, and were carefully observed. It was found that most of the plants irradiated at a rate of 3.0 Krads died. Those plants that were irradiated at a rate of 2.5 Krads exhibited no growth following pinching and were discarded. Many different mutations were observed in the plants that were irradiated at a rate of 1.8 Krads. A single mutation was discovered that exhibited the characteristics of the 'Chafeje' cultivar among these plants, as was a single mutation which exhibited the characteristics of the 'Chanimba' cultivar (copending U.S. Plant patent application Ser. No. 08/710,105). Also, a single mutation that exhibited the characteristics of the 'Chahalu' cultivar (U.S. Plant Pat. No. 9,472), a single mutation that exhibited the characteristics of the 'Chatupa' cultivar (U.S. Plant Pat. No. 9,480), and a single mutation that exhibited the characteristics of the 'Chalurido' cultivar (U.S. Plant Pat. No. 9,502) were discovered among the same group of plants. It would have been impossible for a plant scientist to have predicted in advance that new cultivars having the combination of characteristics of the new 'Chafeje' cultivar and the sister 'Chanimba', 'Chahalu', 'Chatupa', and 'Chalurido' cultivars could have been formed even if the parent 'Chalecat' cultivar would have been available for such experimentation.

It was found that the new cultivar of the present invention:

(a) exhibits attractive large double incurved pompon blossoms that are red in coloration, (b) exhibits a flower response period of approximately ten weeks, (c) forms attractive dark green glossy foliage, (d) achieves a short to medium plant height, and (e) is particularly suited for pot mum production on a recurrent basis throughout the year.

The new cultivar is intended primarily as a decorative pot Chrysanthemum for growing indoors. However, it also can be grown for cut flower production in those instances where stems of approximately 45 cm. or less are acceptable. Also, the new cultivar can be grown outdoors at temperatures above freezing.

In the absence of debudding approximately 11 to 15 blossoms commonly form per stem. The new cultivar can be grown well when single stem or disbudded. An increased number of branches readily can be induced by pinching. The pinching of a cutting commonly produces approximately 3 to 4 stems per cutting. No growth regulator is required to produce the short to medium plant height; however, a growth regulator optionally can be utilized.

The new cultivar can be considered to be an October-flowering greenhouse variety with the natural flowering season commonly occurring in weeks 42 to 43 of the year. Attractive blossoms can be produced on a recurrent basis throughout the year with the indicated ten week response period. The blossoms are long lasting and commonly are maintained attractively on the plant for approximately two weeks.

Asexual reproduction of the new cultivar by cuttings initially taken during 1983, as performed in Nuaille, Trementines, France, in a controlled environment has demonstrated that the characteristics of the new cultivar as herein described are firmly fixed and are retained through successive generations of asexual propagation.

'Chafeje' has not been observed under all possible environmental conditions to date. Accordingly, it is possible that the phenotype may vary somewhat with variations in the environment, such as temperature, light day length, contact with pesticides and/or subjection to growth retardant treatments.

The 'Chafeje' cultivar of the present invention exhibits a combination of characteristics that readily distinguish it from the parent 'Chalecat' cultivar. For instance, the 'Chafeje' cultivar exhibits a red capitulum unlike the 'Chalecat' cultivar, a foliage coloration is near Green Group 139A and sometimes is paler unlike the Yellow-Green Group 147A coloration of the 'Chalecat' cultivar, an angular stem cross-section is exhibited unlike the round stem cross-section of the 'Chalecat' cultivar, a stem coloration of Yellow-Green Group 144A is exhibited unlike the Yellow-Green Group 146B stem coloration of the 'Chalecat' cultivar, and a medium to coarse leaf serration is exhibited unlike the medium to fine leaf serration of the 'Chalecat' cultivar.

As indicated, other mutations of the 'Chalecat' cultivar are the 'Chanimba' cultivar, the 'Chahalu' cultivar, the 'Chatupa' cultivar, and the 'Chalurido' cultivar. Each of these additional cultivars can be readily distinguished from the 'Chafeje' cultivar with respect to a number of plant characteristics.

The 'Chafje' cultivar exhibits a red capitulum unlike the 'Chanimba' cultivar, a foliage coloration of Green Group 139A (and sometime paler) unlike the coloration between Green Group 137A and 147A of the 'Chanimba' cultivar, and an acute and occasionally rounded leaf base unlike the cordate base of the 'Chanimba' cultivar.

The 'Chatupa' cultivar exhibits a honey gold capitulum unlike the 'Chafeje' cultivar, a foliage coloration of the Green Group 137A unlike the coloration of near Green Group 139A and sometimes paler of the 'Chafeje' cultivar, a stem coloration between the Yellow-Green Group 144A and 144B unlike the coloration of Yellow-Green Group 144A of the 'Chafeje' cultivar, a medium leaf serration unlike the medium to coarse leaf serration of the 'Chafeje' cultivar, and a rounded tending to cordate base of the leaves unlike the acute and occasionally rounded leaf base of the 'Chafeje' cultivar.

The 'Chalurido' cultivar exhibits a capitulum having inner surfaces of Venetian violet and outer surfaces of silvery lavender unlike the 'Chanimba' cultivar, a foliage coloration of the Yellow-Green Group 147A unlike the foliage coloration that is near the Green Group 139A and sometimes paler of the 'Chafeje' cultivar, a fine to coarse leaf serration unlike the medium to coarse leaf serration of the 'Chafeje' cultivar, and an asymmetric base of the leaf unlike the acute and occasionally rounded leaf base of the 'Chafeje' cultivar.

The 'Chahalu' cultivar exhibits a yellow capitulum unlike the 'Chafeje' cultivar, no anthocyanin coloration on the stem unlike the 'Chafeje' cultivar, a fine to coarse leaf serration unlike the medium to coarse leaf serration of the 'Chafeje' cultivar, and a diverging margin of sinus between lateral leaf lobes unlike the converging margin of the 'Chafeje' cultivar.

The new 'Chafeje' cultivar is being marketed under the RED CYMBAL trademark.

BRIEF DESCRIPTION OF THE PHOTOGRAPH

The accompanying photograph was prepared during March, 1996, and shows as nearly true as it reasonably possible to make the same a color illustration of this character, typical plants and plant parts of the new cultivar of the present invention. The plants were twelve weeks of age and were grown in Nuaille, Trementines, France, under standard greenhouse conditions which approximate those commonly utilized for the production of decorative pot mums. The plants had been disbudded except where indicated in order to encourage the formation of one bloom per stem.

FIG. 1 illustrates the upper surface of a typical leaf from the lower part of the stem;

FIG. 2 illustrates the under surface of a typical leaf from the lower part of the stem;

FIG. 3 illustrates the upper surface of a typical leaf from the upper part of the stem;

FIG. 4 illustrates the under surface of a typical leaf from the upper part of the stem;

FIG. 5 illustrates the side view of an unopened bud;

FIG. 6 illustrates the side view of a bud when opening;

FIG. 7 illustrates a side view of a flower during the course of opening;

FIG. 8 illustrates an obverse view of a fully expanded flower;

FIG. 11 illustrates the top view of three typical outer ray-florets;

FIG. 12 illustrates the side view of three typical outer ray-florets;

FIG. 13 illustrates the top view of three typical inner ray florets;

DETAILED DESCRIPTION

Figures 9, 10, 14, 15:
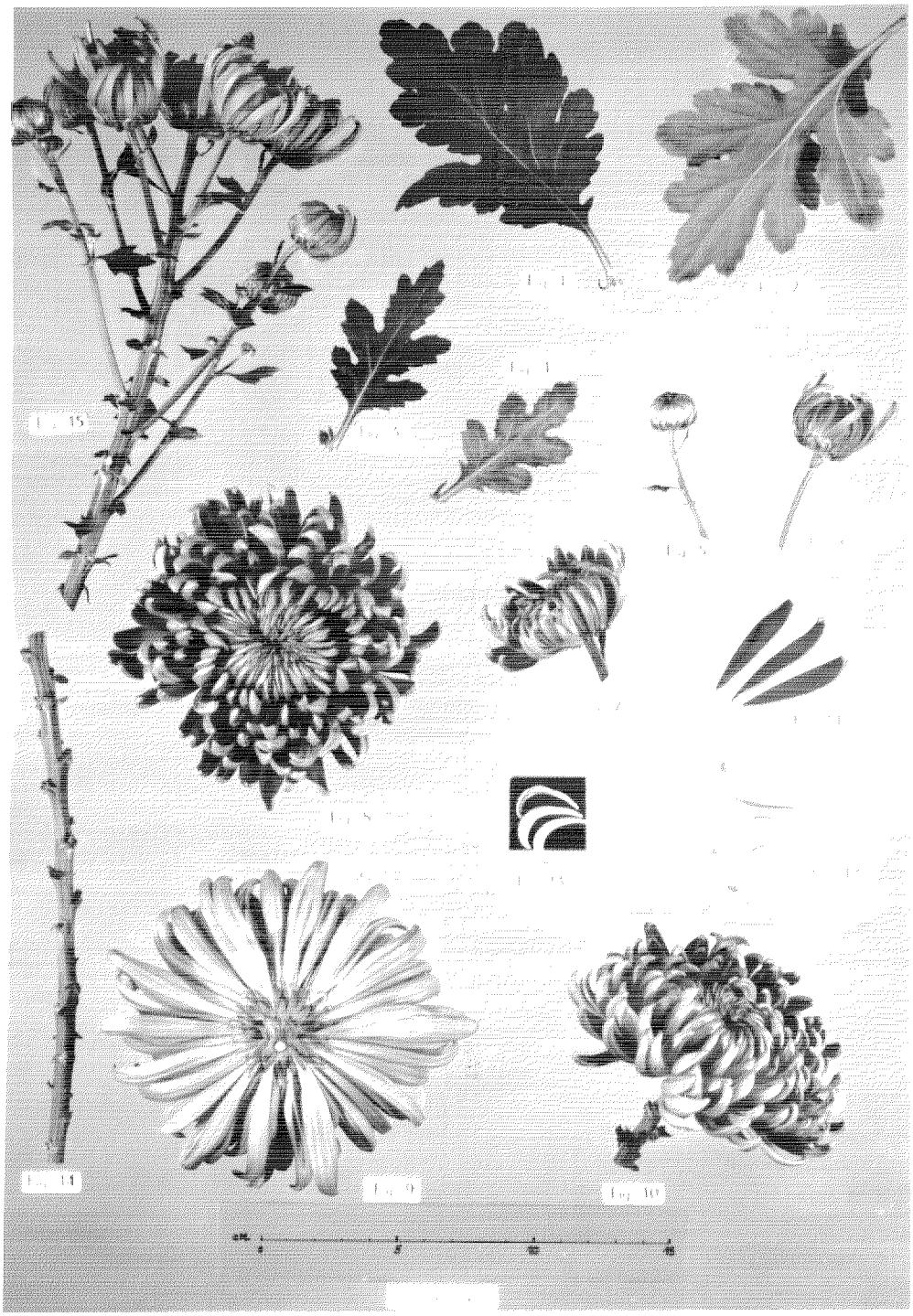
FIG. 9 illustrates a reverse view of a fully expanded flower.
FIG. 10 illustrates the side view of a fully expanded flower.
FIG. 14 illustrates a stem.
FIG. 15 illustrates a side of typical inflorescence in the absence of disbudding.

The chart used in the identification of colors described hereafter is the R.H.S. Colour Chart of The Royal Horticultural Society, London, England. In some instances more common color terms are provided and are to be accorded their usual dictionary significance. The plants described were grown at Naille, Trementines, France, in 20 cm. pots, three plants to a pot, were rooted in early June, and were stopped during mid-July. All primary laterals were retained. Disbudding was carried out to leave the terminal flower heads, the plants were grown outdoors until late September, and then were grown in greenhouses having a minimum temperature of 15.5° C. These conditions approximate those commonly utilized for the production of decorative pot mums.

Classification:

*Botanical.*—*Dendranthema grandiflora*, cv. 'Chafeje'.
*Commercial.*—Decorative pot mum.

Inflorescence

A. Capitulum:

*Form.*—Large, double, incurved, and commonly exhibiting a perfect configuration. The incurving commonly is particularly strong at the tips.

*Type.*—Pompom.

*Diameter across face.*—Approximately 12 to 14 cm. on average when fully expanded.

B. Corolla of ray and disc florets:

*Color of bud.*—Greyed-Orange Group 173D but redder and becoming paler towards the base.

*Disc florets.*—Tubular, few in number, very difficult to observe, and tend to be scattered among the ray florets with a small cluster at the apex of the receptacle that is visible only when the ray florets are removed.

*General tonality.*—Red.

*Color ray florets.*—When the flowers are fully expanded, the outer surfaces of most florets of the outer row are Yellow-Orange Group 19C tinged with Greyed-Purple Group 186B and sometimes redder between ribs. When the flower is fully expanded, the inner surfaces of most florets of the outer row of florets are Yellow-Orange Group 19C tinged with Greyed-Purple Group 186B, but yellower at the base, and sometimes giving an overall impression of Red 48C but redder. When the outer row of florets is fully expanded, the outer surfaces of the inner florets are Yellow-Orange Group 19C tinged with Greyed-Purple Group 186B, and sometimes redder between the ribs but paler and yellower than the coloration of most florets.

*Configuration ray petals.*—The longitudinal axis of most petals incurves distally with a medium degree of curvation. The longitudinal axis of the outer row of petals strongly incurves distally. The cross-section of the ray florets is concave, and sometimes is flat. The length of the corolla tube is short. The thickness of the ray florets is medium, and their surfaces are textured. The tips of the ray florets are dentate and occasionally are pointed. The ray florets commonly are approximately 60 mm. in length and approximately 10 mm. in width on average.

C. Reproductive organs:

*Androcium.*—Generally present with the disc florets and absent in the ray florets.

*Gynoecium.*—Generally present with most disc florets and with most ray florets.

*Pollen.*—Formed in a sparse quantity and golden-yellow in coloration.

*Fragrance.*—Typical of Chrysanthemum.

Plant

A. General appearance:

*Height.*—Short to medium, and approximately 40 to 45 cm. in height on average.

B. Foliage:

*Color.*—Nearest Green Group 139A, and sometimes paler.

*Configuration.*—Lobed (as illustrated).

*Texture.*—Fleshy.

*Serration.*—Medium to coarse.

*Length of lower lobe.*—Medium.

*Shape of base.*—Acute, and occasionally rounded.

*Claw in base of sinus between lateral lobes.*—Present.

*Margins of sinus between lateral lobes.*—Converging.

*Apex.*—Mucronate.

*Stems.*—Strong, angular in cross section, nearest to Yellow-Green Group 144A in coloration, and having anthocyanin coloration.

I claim:

1. A new and distinct cultivar of Chrysanthemum plant named 'Chafeje', substantially as herein shown and described, which (a) exhibits attractive large double incurved pompon blossoms that are red in coloration,
(b) exhibits a flower response period of approximately ten weeks,
(c) forms attractive dark green glossy foliage,
(d) achieves a short to medium plant height, and
(e) is particularly suited for pot mum production on a recurrent basis throughout the year.

* * * * *